United States Patent
Connor et al.

(10) Patent No.: US 8,715,252 B2
(45) Date of Patent: May 6, 2014

(54) APPARATUS FOR APPLYING ROLL-ON AND RUB-ON MEDICATIONS

(75) Inventors: Richard Dale Wayne Connor, Merritt Island, FL (US); Ronald Lowell Franklin Connor, Crestview, FL (US)

(73) Assignee: Richard Dale Wayne Connor, Merritt Island, FL (US)

( * ) Notice: Subject to any disclaimer, the term of this patent is extended or adjusted under 35 U.S.C. 154(b) by 0 days.

(21) Appl. No.: 13/615,869

(22) Filed: Sep. 14, 2012

(65) Prior Publication Data

US 2014/0081220 A1   Mar. 20, 2014

(51) Int. Cl.
*A61M 35/00* (2006.01)

(52) U.S. Cl.
USPC .......................................... 604/289; 206/581

(58) Field of Classification Search
CPC ......... A47K 7/028; A47K 7/022; A47K 7/04; A47K 7/06; A47K 7/00; A47K 5/00; A47K 11/10; A45D 33/00; A45D 2200/1081; A45D 34/04; A45D 34/041; A61M 35/003; B05C 17/0205
USPC ............ 15/244.2, 144.4, 244.1, 210.1, 143.1, 15/147.1, 148, 153, 231; 138/95, 97; 604/289; 16/421, 429, 430; 607/89, 88; 606/13, 19; 206/581
See application file for complete search history.

(56) References Cited

U.S. PATENT DOCUMENTS

| | | | | | |
|---|---|---|---|---|---|
| 4,299,005 | A | * | 11/1981 | Brown | 15/244.2 |
| 5,312,097 | A | * | 5/1994 | Womack | 269/139 |
| 5,658,065 | A | * | 8/1997 | Jamieson | 362/106 |
| 6,484,406 | B1 | * | 11/2002 | Gardner | 30/310 |
| 7,334,286 | B2 | * | 2/2008 | Kayser | 15/167.1 |
| 7,377,403 | B2 | * | 5/2008 | Gorrie | 222/103 |
| 8,151,828 | B2 | * | 4/2012 | Parton | 138/99 |
| 2007/0177928 | A1 | * | 8/2007 | Aarhaus | 401/123 |
| 2008/0173600 | A1 | * | 7/2008 | Mungal | 211/71.01 |
| 2009/0159487 | A1 | * | 6/2009 | Tacoma | 206/581 |
| 2012/0099333 | A1 | * | 4/2012 | Wang | 362/396 |

FOREIGN PATENT DOCUMENTS

GB             1030909      *   5/1966

* cited by examiner

*Primary Examiner* — Philip R Wiest
*Assistant Examiner* — Ariana Zimbouski
(74) *Attorney, Agent, or Firm* — Lyman Smith

(57) ABSTRACT

A clamp and handle is designed exclusively for holding purchased containers of rub on and roll on pain killers, deodorants and any other substance that is in a container with a built in applicator. The handle is for applying these substances to hard or impossible places to reach due to anatomy or injury. The clamp, handle and knob are constructed from PVC that has a smooth glossy finish for the purpose of not causing any injury. The PVC can move smoothly over skin. The knob is flower shaped to make it easier to grip. The knob and clamp body prevent the stainless steel screw from scratching any skin. The screw will never rust.

13 Claims, 2 Drawing Sheets

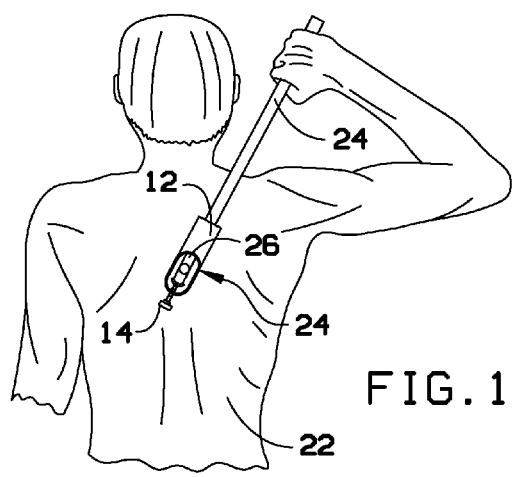
FIG. 1
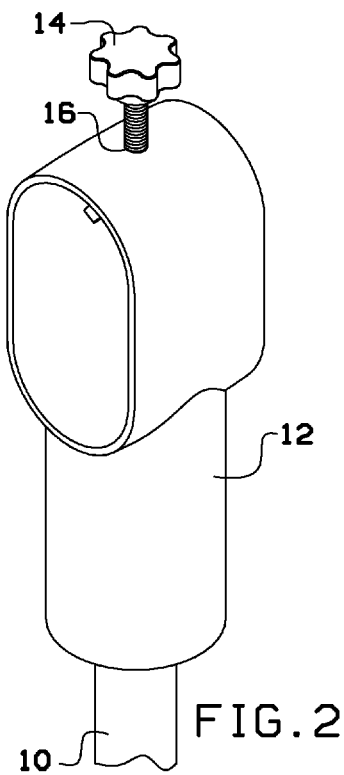
FIG. 2
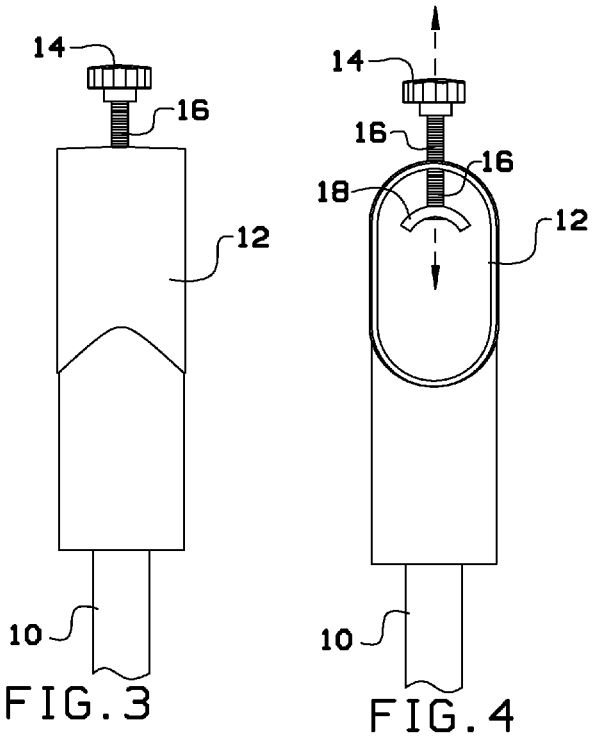
FIG. 3
FIG. 4
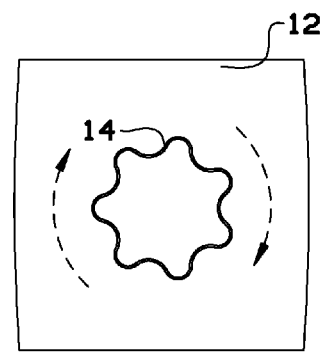
FIG. 5

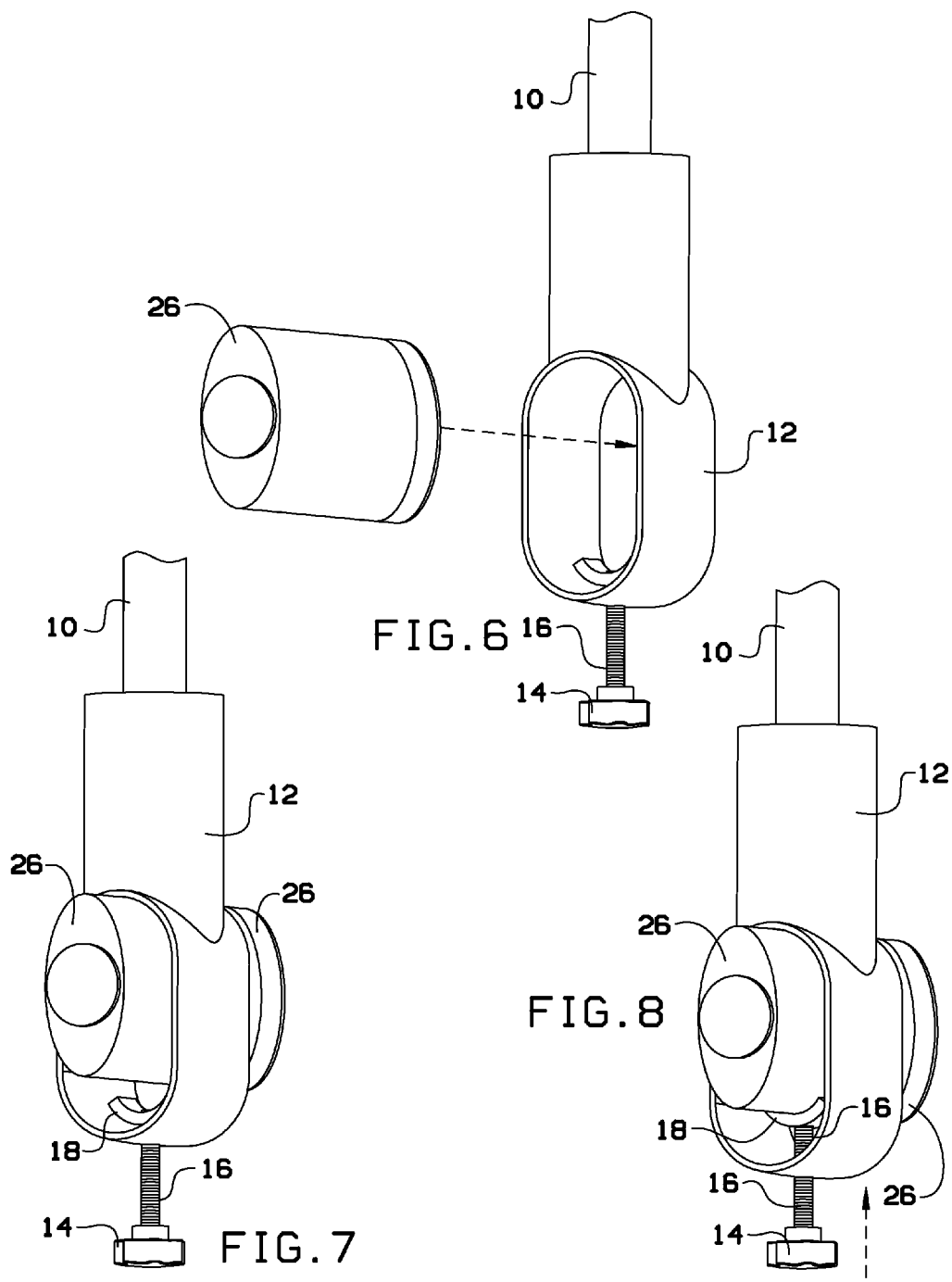

APPARATUS FOR APPLYING ROLL-ON AND RUB-ON MEDICATIONS

BACKGROUND OF THE INVENTION

The present invention relates to the art of helping people to apply store bought products to hard to reach areas of the body without causing any injury to those people.

Conventional roll-on or rub-on products are packaged in plastic containers with their own applicators and caps. People can have difficulty holding these types of containers and applying the contents to hard to reach areas of the body. For people that live alone that may have, for example, a sore back, their pain relief solutions may be limited when they cannot reach the affected area to apply a topical pain relief product.

As can be seen, there is a need for a device that can safely grip a roll-on or rub-on product to apply that product in hard to reach locations of the body.

BRIEF SUMMARY OF THE INVENTION

The present invention includes an O-clamp with an elongated handle. The clamp is used to hold a variety of products packaged in containers with their own applicators and caps. The handle allows a person's product to be applied to areas of their body they cannot reach due to anatomy or injury. The invention is primarily made of furniture grade PVC which is extremely smooth for the purpose of not causing injury to the user's skin.

BRIEF DESCRIPTION OF THE DRAWINGS

FIG. 1 is a perspective view of an exemplary embodiment of an apparatus for applying roll-on and rub-on medications;

FIG. 2 is a perspective view of the apparatus of FIG. 1;

FIG. 3 is a side view of the apparatus of FIG. 1;

FIG. 4 is a front view of the apparatus of FIG. 1;

FIG. 5 is a top view of the apparatus of FIG. 1;

FIG. 6 is a perspective view of the apparatus of FIG. 1 in a pre-insertion phase of a container of roll-on or rub-on medication into the clamp body;

FIG. 7 is a perspective view of the apparatus of FIG. 1 in post-insertion phase of the container into the clamp body; and FIG. 8 is a perspective view of the apparatus of FIG. 1 illustrating the container securely held in the clamp body.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention generally provides an apparatus for applying roll-on and rub-on medications to one's body, such as to areas that are difficult to reach. The apparatus may include a rigid handle 10 with an elongated open clamp body 12 on one end (FIGS. 1, 2, and 3). A clamp screw 16 may be threaded through an opening in the end of the clamp body 12. The clamp screw 16 may have a knob 14 on the end of the screw that remains outside the clamp body 12 and a clamp saddle 18 on the end of the screw head that is inside the clamp body 12 (FIG. 4). As the knob 14 is turned (FIG. 5) in a clockwise direction, the clamp screw 16 moves farther into the clamp body 12, pushing the clamp saddle 18 with it. Turning the knob 14 in the opposite direction moves the clamp screw 16 out of the clamp body 12.

The handle 10 may be any length and any diameter but about 18 inches may be a convenient length and about ¾ of an inch may be a convenient diameter for many people. The handle 10 may be made from any appropriate material, such as wood, plastic, or furniture-grade PVC (which has the benefit of being very smooth), and may have a grip made from rubber or other like material on the end. The clamp body 12 may also be made from any appropriate material, such as furniture-grade PVC, and may be about 5 inches long. The clamp saddle 18 may be at least somewhat flexible and made from a section of ¾-inch flexible PVC pipe. Alternatively, the clamp body 12 may be injection molded plastic. The saddle 18 may be made from injection molded flexible PVC or alternative stiff rubber. The clamp screw 16 may be a ¼"-20 oval head stainless steel screw. One end of the clamp screw 16 may be inserted through a hole in the clamp saddle 18 and loosely held in place with a stainless steel lock nut so that the clamp saddle 18 may move independent of the clamp screw 18. The other end of the clamp screw 16 may be threaded through the top of the clamp body 12 and screwed into the knob 14. One end of the handle 10 may be pressure-fitted into the bottom of the clamp body 12 and the other end of the handle 10 may be pressed into a cap, such as a PVC cap.

To use, a person may insert a roll-on or rub-on medication container 26 into the clamp body 12 (FIG. 6). Medications such as Icy Hot and Max-Freeze are sold as roll-on and rub on medications in containers that may be used with the apparatus of the present invention. The person may turn the knob 14 to move the clamp saddle 18 towards the medication container 26 (FIG. 7) until the clamp saddle 18 rests firmly against the outside of the medication container 26 (FIG. 8). In this way, the medication container 26 may be held securely between the clamp saddle 18 and the inside of the clamp body 12 at approximately a 90 degree angle with the medication facing out from the clamp body 12. The user may then hold the handle 10 in one hand and move the apparatus so that the medication in the container 26 can be applied to an area 24 of the person's body that is otherwise hard to reach, such as the middle or upper back (FIG. 1) or to the lower leg. The apparatus may be particularly useful to those who live alone or otherwise have no help applying roll-on or rub-on medications. The configuration of the clamp body 12 may allow the user to turn a knob on the end of the medication container 26 to advance the medication out from the container 26.

The apparatus may also be used to hold other items within the clamp body 12.

It should be understood, of course, that the foregoing relates to exemplary embodiments of the invention and that modifications may be made without departing from the spirit and scope of the invention as set forth in the following claims.

What is claimed is:

1. An apparatus for applying roll-on and rub-on medications, comprising
    an elongated handle;
    a clamp body formed as an integral member that completely surrounds an opening, the opening having at least one arc-shaped inside surface configured to receive a container of roll-on or rub-on medication;
    a screw threaded through an opening in the clamp body and having a threaded end that remains outside the clamp body and a screw head end that is inside the clamp body;
    a knob on the threaded end of the screw; and
    a clamp saddle having a hole through which the screw passes entirely through the clamp saddle, the clamp saddle being loosely held in place directly at the screw head end of the screw such that the clamp saddle can move longitudinally within the clamp body as the screw rotates, the clamp saddle having an arc-shape operable to secure against the container of roll-on or rub-on medication, the clamp saddle disposed inside the opening;

whereby, when the container of medication is inserted into the clamp body and the knob is turned, the container becomes securely held directly between the clamp saddle and the clamp body and the medication is capable of being applied to hard to reach areas of a body.

2. The apparatus of claim 1, wherein the opening is shaped as an elongated ellipse.

3. The apparatus of claim 1, wherein the clamp body includes threads operable to receive threads of the screw.

4. The apparatus of claim 1, wherein the clamp saddle is made from a flexible material.

5. The apparatus of claim 1, wherein the clamp saddle is made from flexible PVC.

6. The apparatus of claim 1, wherein the clamp saddle moves independently of the screw.

7. The apparatus of claim 1, wherein the elongated handle is pressure fitted into the clamp body.

8. The apparatus of claim 1, wherein the opening of the clamp body permits access to a top end and a bottom end of the container of roll-on or rub-on medication.

9. An apparatus comprising
an elongated handle;
a clamp body, the clamp body formed as an integral member that completely surrounds an opening, the opening having at least one arc-shaped inside surface configured to receive a container;
a screw threaded through a threaded opening in the clamp body, the screw having a threaded end that remains outside the clamp body and a screw head end that extends inside the clamp body;
a knob on the threaded end of the screw; and
a clamp saddle having a hole through which the screw passes entirely through the clamp saddle, the clamp saddle being loosely held in place directly at the screw head end of the screw, the clamp saddle having a flexible arc-shape operable to secure against the container, the clamp saddle disposed inside the opening, wherein the opening of the clamp body permits access to a top end and a bottom end of the container.

10. The apparatus of claim 9, wherein the opening is shaped as an elongated ellipse.

11. The apparatus of claim 9, wherein the clamp saddle is made from flexible PVC.

12. The apparatus of claim 9, wherein the clamp saddle moves independently of the screw.

13. The apparatus of claim 9, wherein the elongated handle is pressure fitted into the clamp body.

* * * * *